United States Patent [19]

Autin et al.

[11] Patent Number: 5,254,554
[45] Date of Patent: Oct. 19, 1993

[54] 3-HYDROXY-SUBSTITUTED-1-PHENYL-1,4-DIHYDRO-4-OXOPYRIDAZINES AND DERIVATIVES, AND USE

[75] Inventors: Jean-Marie Autin, Labruguiere; Dennis Bigg; Jean-Francois Patoiseau, both of Castres, all of France

[73] Assignee: Pierre Fabre Medicament, Boulogne, France

[21] Appl. No.: 886,341

[22] Filed: May 20, 1992

[30] Foreign Application Priority Data

May 22, 1991 [FR] France ................... 91 06148

[51] Int. Cl.$^5$ ............................................. C07D 237/22
[52] U.S. Cl. ................................... 514/253; 514/247; 514/252; 544/238; 544/240
[58] Field of Search ............... 544/240, 238; 514/252, 514/247, 253

[56] References Cited

U.S. PATENT DOCUMENTS

| | | | |
|---|---|---|---|
| 2,792,396 | 5/1957 | Druey et al. | 544/238 |
| 2,835,671 | 5/1958 | Staehlin et al. | 544/239 |
| 4,561,881 | 12/1985 | Labovitz et al. | 544/238 |
| 4,672,063 | 6/1987 | Jasserand | 514/252 |
| 5,059,599 | 10/1991 | Mouzin et al. | 544/239 |

FOREIGN PATENT DOCUMENTS 0402227 12/1990 European Pat. Off. .
2383605 3/1978 France .

OTHER PUBLICATIONS

Staehelin et al. Chem. Abstr. vol. 51 entry 4380d (1957).
Plescia et al. J. Hetero. Chem. vol. 18, pp. 333-334 (1981).
Helvetica Chimica Acta 39, No. 206-207, pp. 1741-1754 (1956) authored by von A. Staehelin, K. Eichenberger and J. Druey.
Chemical Abstracts, vol. 58, No. 5, 4539-4540 (1962).

*Primary Examiner*—Donald G. Daus
*Attorney, Agent, or Firm*—Gordon W. Hueschen

[57] ABSTRACT

The application discloses pharmacologically-active 3-hydroxy-1-phenyl-1,4-dihydro-4-oxopyridazine compounds, derivatives thereof, a method for the preparation thereof, pharmaceutical compositions thereof, and a method of treating anxiety and other physiological abnormalities therewith.

6 Claims, No Drawings

3-HYDROXY-SUBSTITUTED-1-PHENYL-1,4-DIHYDRO-4-OXOPYRIDAZINES AND DERIVATIVES, AND USE

FIELD OF THE INVENTION

The present invention has as its object new and valuable pharmacologically-active 1,3-disubstituted-4-oxo-1,4-dihydropyridazine compounds which are optionally substituted at position 6, a process for their preparation, pharmaceutical compositions thereof, and a method of treating therewith.

BACKGROUND OF THE INVENTION AND PRIOR ART

Some 1-phenyl-1,4-dihydro-4-oxopyridazines, variously substituted at position 3, are described in the literature. Among these compounds, the carboxylic acids exhibit a plant growth regulant activity and are used as gametocides (French patent application FR-A-2,383,605, Rohm and Haas Company). Other acids, variously substituted on the aromatic ring, and their esters, have an activity which stimulates the central nervous system (U.S. Pat. Nos. 2,792,396 and 2,835,671, Ciba Pharmaceutical Products). Compounds aminated at position 3, with an activity on the central nervous system, have already been described by the applicant (French patent application FR-A-2,648,135, Pierre Fabre Medicament) (published Sep. 27, 1991). See also corresponding EPA 0 402 227, published Dec. 12, 1990 and U.S. Pat. No. 5,059,599, issued Oct. 22, 1991. In addition, 1-phenyl-1,4-dihydro-3-hydroxy-4-oxopyridazine has been synthesized by Stahelin et al. (Helv. Chim. Acta 39 1741–1754, 1956), who do not mention any pharmacological activity.

OBJECTS OF THE INVENTION

It is an object of the invention to provide novel 1,3-disubstituted-4-oxo-1,4-dihydropyridazine compounds, a method of preparation of the same, pharmaceutical compositions thereof, and a method of treating various physiological abnormalities therewith. Additional objects will become apparent hereinafter, and still others will be obvious to one skilled in the art to which this invention pertains.

SUMMARY OF THE INVENTION

The invention, the, comprises the following, inter alia, singly or in comination:

A compound selected from a 3-substituted-1-phenyl-1,4-dihydro-4-oxopyridazine of Formula I:

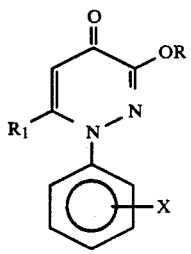

in which:
"X" represents one or more substituents selected from $C_{1-4}$ alkyloxy, halogen, and trifluoromethyl;
"$R_1$" represents hydrogen or $C_{1-3}$ lower-alkyl;
"R" represents:
hydrogen;
$C_{1-4}$ lower-alkyl or $C_{2-4}$ alkenyl;
$C_{1-4}$ lower-acyl; or
aminoalkyl of Formula II:

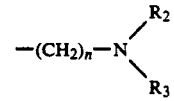

in which
"n" is 2 to 4, inclusive, and
"$R_2$" and "$R_3$", identical or different, represent hydrogen or $C_{1-4}$ lower-alkyl;
phenyl $C_{1-4}$ alkyl, optionally substituted in the aromatic ring by one or more substituents selected from $C_{1-3}$ alkyl, $C_{1-3}$ alkyloxy, halogen, and trifluoromethyl; and
arylmethyl, wherein aryl is selected from 2-pyridyl, 3-pyridyl, 4-pyridyl, and 2-quinolinyl, and a pharmaceutically-acceptable salt thereof when R contains a salt-forming group;
such a compound selected from the group consisting of:
1-Metatrifluoromethylphenyl-1,4-dihydro-3-hydroxy-4-oxo-6-methylpyridazine;
1-Metatrifluoromethylphenyl-1,4-dihydro-3-methoxy-4-oxo-6-methylpyridazine;
1-Metatrifluoromethylphenyl-1,4-dihydro-3-acetoxy-4-oxo-6-methylpyridazine;
1-Metatrifluoromethylphenyl-1,4-dihydro-3-ethoxy-4-oxo-6-methylpyridazine;
1-Metatrifluoromethylphenyl-1,4-dihydro-3-allyloxy-4-oxo-6-methylpyridazine;
1-Metatrifluoromethylphenyl-1,4-dihydro-3-benzyloxy-4-oxo-6-methylpyridazine;
1-Metatrifluoromethylphenyl-1,4-dihydro-3-$\beta$-aminoethoxy-4-oxo-6-methylpyridazine;
1-Metatrifluoromethylphenyl-1,4-dihydro-3-$\beta$-dimethylaminoethoxy-4-oxo-6-methylpyridazine;
1-Metatrifluoromethylphenyl-1,4-dihydro-3-methoxy-4-oxopyridazine;
1-Metatrifluoromethylphenyl-1,4-dihydro-3-benzyloxy-4-oxopyridazine;
1-Metatrifluoromethylphenyl-1,4-dihydro-3-(2-quinolylmethoxy)-4-oxo-6-methylpyridazine;
1-Metachlorophenyl-1,4-dihydro-3-methoxy-4-oxo-6-methylpyridazine;
1-Metatolyl-1,4-dihydro-3-methoxy-4-oxo-6-methylpyridazine;
1-Metafluorophenyl-1,4-dihydro-3-(2-quinolylmethoxy)-4-oxo-6-methylpyridazine;
1-Parafluorophenyl-1,4-dihydro-3-(2-quinolylmethoxy)-4-oxo-6-methylpyridazine;
1-(3,4-Dimethoxy)phenyl-1,4-dihydro-3-methoxy-4-oxo-pyridazine;
1-(3,4,5-Trimethoxy)phenyl-1,4-dihydro-3-methoxy-4-oxo-pyridazine;
1-(3,4,5-Trimethoxy)phenyl-1,4-dihydro-3-methoxy-4-oxo-6-methylpyridazine; and a pharmaceutical composition useful for the treatment of anxiety which contains, as active principle, an amount of such compound which is effective for such purpose together with a pharmaceutically-acceptable diluent or carrier; as well as a method of treating anxiety in a mammal afflicted therewith, comprising the step of administering to said mammal an amount of a compound which is effective for such purpose.

Further, a process for the preparation of such compound wherein a 3-aminopyridazine of Formula IIIa, wherein $R_1$ and X have the meanings assigned is treated with sodium nitrite in a hydrochloric environment, or with an organic nitrite such as tertiobutyl nitrite in a solvent or a mixture of solvents, such as water-DMF, in order to convert the amino group to a hydroxy group, and the 3-hydroxypyridazine thus obtained is then reacted with a compound RX, wherein "R" has the meaning assigned and "X" represents a halogen, selected from iodine, chlorine, and bromine, or with a dialkyl sulfate $(R)_2SO_4$, a mesylate, or a tosylate; such a process wherein the reaction is carried out in the presence of a base selected from NaH and NaOH; such a process wherein the reaction is carried out in a solvent selected from DMF, DMSO, dimethyl acetamide (DMA), and tetrahydrofurane (THF); such a process wherein the reaction is carried out in a biphasic environment in the presence of a phase-transfer catalyst; such a process wherein the biphasic environment is provided by a combination of soda and THF. Moreover, a process for the preparation of such compound wherein a 3-chloropyridazine of Formula IIIb is reacted with an alcohol ROH, wherein "X", "$R_1$" and "R" have the same meanings as assigned; and finally such a process as just recited wherein the reaction is carried out in the presence of a base selected from NaH and KOH in a solvent selected from DMF, DMSO, and THF.

GENERAL DESCRIPTION OF THE INVENTION

The new chemical compounds of the present invention correspond to Formula I:

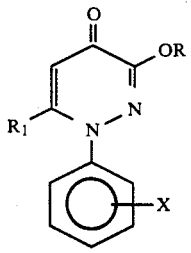

I in which:
"X" represents one or more substituents selected from $C_{1-4}$ lower-alkyl, $C_{1-4}$ alkyloxy, halogen, and trifluoromethyl;
"$R_1$" represents hydrogen or $C_{1-4}$ lower-alkyl;
"R" represents:
hydrogen;
$C_{1-4}$ lower-alkyl or $C_{2-4}$ lower-alkenyl;
$C_{1-4}$ lower-acyl; and
amino-alkyl of Formula II:

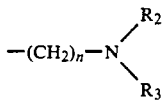

II in which "n" is 2 to 4, inclusive, and

"$R_2$" and "$R_3$", identical or different, represent hydrogen or $C_{1-4}$ lower-alkyl;
$C_{1-4}$ phenyl-alkyl optionally substituted in the aromatic ring by one or more substituents selected from $C_{1-3}$ alkyl, $C_{1-3}$ alkyloxy, halogen, and trifluoromethyl; or
arylmethyl, wherein aryl is selected from 2-pyridyl, 3-pyridyl, 4-pyridyl, and 2-quinolinyl.

The invention also includes the pharmaceutically-acceptable organic or mineral salts of the compounds which include a salifiable function. The present invention likewise concerns the preparation of compounds of Formula I from 1-phenyl-3-amino-4-oxopyridazines of Formula IIIa or 1-aryl-3-chloro-4-oxopyridazine of Formula IIIb, wherein "X" and "$R_1$" have the same meaning as in Formula I. These intermediate compounds may be obtained in accordance with the disclosure of French patent application FR-A-2,648,135, of Pierre Fabre Medicament (published Sep. 27, 1991).

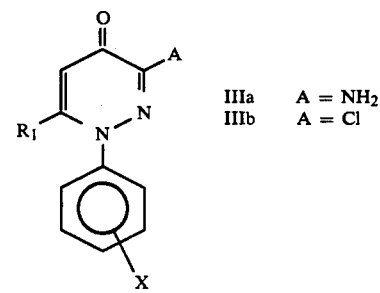

IIIa  A = $NH_2$
IIIb  A = Cl

Such process, starting from the amino derivative IIIa, comprises:

a) A first stage which consists of converting the amine into a hydroxylated derivative by treatment with sodium nitrite in a hydrochloric acid environment, or with an organic nitrite such as tertiobutyl nitrite in a solvent such as mixture of water and dimethyl formamide;

b) A second stage of O-alkylation using an "RX" derivative, with "R" having the same meaning as above, and "X" representing a labile or leaving group, such as chlorine, bromine, or iodine, or using a dialkyl sulfate $(R)_2SO_4$, a mesylate, or a tosylate. This reaction may best be carried out in the presence of a base such as, for example, NaH or NaOH, in a suitable solvent, such as DMF, DMSO, THF, or dimethyl acetamide (DMA).

The reaction may be advantageously carried out in a biphasic environment, such as represented by THF-soda, in the presence of a phase-transfer catalyst, such as tetrabutyl ammonium bromide.

In the event that the "R" radical includes a functional group, such as a primary amine, the function may be temporarily blocked in known manner in the form of a phthalimide, and the desired product may be obtained in accordance with the classical methods of deprotection, such as treatment with hydrazine, ethanolamine, or ethylene diamine.

Such process, starting from the chloro derivative IIIb, consists of reacting the chloro derivative with an alcohol ROH in the presence of a base, such as, by way of example, NaH or KOH, in a suitable solvent, such as DMF, DMSO or THF.

DETAILED DESCRIPTION OF THE INVENTION

The following examples illustrate the present invention, but are not to be construed as limiting. The elemental analyses, as well as the IR and NMR spectra, confirm the structure of the compounds obtained.

EXAMPLE 1

1-m.trifluoromethylphenyl-1,4-dihydro-3-hydroxy-4-oxo-6methylpyridazine (Compound 1)

A suspension of 1-m.trifluoromethylphenyl-1,4-dihydro-3-amino-4-oxo-6-methylpyridazine (21 grams, 0.078 mole) in 400 ml of water is chilled. After the addition of 12N hydrochloric acid (14.5 ml), sodium nitrite (5.38 g) is added, drop by drop, with 50ml of water. After agitation of the mixture for one hour at 0° C., two hours at 20° C., and then ten minutes at 50° C., it is rechilled, filtered through sintered glass, and washed with water. The precipitate is dissolved in 1200 ml of tepid ethyl acetate. After drying over sodium sulfate, filtration and evaporation under vacuum, the product crystallizes after being dissolved in diethyl ether. There is obtained, after recrystallization from a 75/25 mixture of dioxane and diethyl ether, the Compound 1 (18.75 grams; yield=90%).

MP=242° C.;

CCM (thin-layer chromatography): Rf=0.21 (chloroformmethanol: 85/15).

EXAMPLE 2

1-m.trifluoromethylphenyl-1,4-dihydro-3-methoxy-4-oxo-6-methylpyridazine (Compound 2)

Tetrabutylammonium bromide (635 mg), 6N soda (13 ml), and methyl sulfate (5.59 ml) are added to a solution of Compound 1 (5.31 grams) in THF. After 1 hour 30 minutes of stirring at 25° C., the solution is evaporated under vacuum, dissolved in water, and extracted with ethyl acetate. After washing with water, drying, filtration and evaporation under vacuum, a residue is obtained which is dissolved in ether and recrystallized from a 60/40 mixture of dioxane and hexane, to provide Compound 2 (3.97 grams; yield 71%).

MP=172° C.

CCM: Rf=0.39 (CHCl$_3$-MeOH: 85/15).

EXAMPLE 3

1-m.trifluoromethylphenyl-1,4-dihydro-3-acetoxy-4-oxo-6-methylpyridazine (Compound 3)

A suspension of Compound 1 (2.36 grams) in acetic anhydride is heated for six hours at 50° C. The recooled solution is concentrated under vacuum. There is obtained, after the addition of diethyl ether, filtration, washing with ether and drying, the Compound 3 (1.91 grams; yield=70%).

MP=153°-154° C.

CCM: Rf=0.77 (methanol-chloroform: 15/85).

EXAMPLE 4

1-m.trifluoromethylphenyl-1,4-dihydro-3-β-aminoethoxy-4-oxo-6-methylpyridazine (Compound 7)

Compound 1 (1.35 grams) is added to a suspension of sodium hydride (0.084 grams) in dimethylacetamide (14 ml). 1-Bromo-2-phthalimidoethane (2.54 grams) is then introduced, and agitation is carried out for three hours at 120° C. After evaporation under vacuum of the dimethylacetamide, the reaction mixture is diluted with water and extracted with ethyl acetate. The organic solution is washed with 2N soda and then with water, dried over sodium sulfate, filtered and concentrated. There are obtained, upon cooling, 1.26 grams of white crystals comprising the intermediate phthalimide derivative.

This compound (1.09 grams) is dissolved with ethylene diamine (7 ml) and agitated for four hours at ambient temperature. After evaporation of the ethylene diamine under vacuum, the residue is dissolved in water and extracted with ethyl acetate.

After drying over sodium sulfate, filtration and concentration to dryness, there is obtained, after recrystallization from diethyl ether, the Compound 7 (0.67 grams; total yield=49%).

MP=160° C.

CCM: Rf=0.70 (methanol-chloroform: 15/85).

EXAMPLE 5

1-m.trifluoromethylphenyl-1,4-dihydro-4-oxo-3-(2-methoxyquinolyl)-6-methylpyridazine (Compound 11)

A solution of 2-hydroxymethyl quinoline(1.34 grams) in THF (20 ml) is brought to 0° C. Sodium hydride (0.34 grams) is added in small portions and then, after thirty minutes, there is added 1-m.trifluoromethylphenyl-1,4-dihydro-3-chloro-4-oxo-6-methylpyridazine (2.08 grams). After thirty minutes at 0° C. and four hours at ambient temperature, the reaction mixture is concentrated to dryness, dissolved into water and extracted with ethyl acetate. The organic phase is washed with water, dried over sodium sulfate, filtered, and concentrated to dryness under vacuum.

The Compound 11 (1.35 grams; yield=39%) is obtained after purification by flash chromatography (eluant CHCl$_3$-MeOH: 95/5).

MP=189° C.

CCM: Rf=0.4 (CHCl$_3$-MeOH: 95/5).

The following table summarizes the primary products synthesized, which illustrate the invention without limiting the scope of the same.

| N' | X | R$_1$ | R | MP, °C. |
|---|---|---|---|---|
| 1 | m.CF$_3$ | CH$_3$ | H | 242 |
| 2 | m.CF$_3$ | CH$_3$ | CH$_3$ | 172 |
| 3 | m.CF$_3$ | CH$_3$ | COCH$_3$ | 153-154 |
| 4 | m.CF$_3$ | CH$_3$ | CH$_2$CH$_3$ | 158-159 |
| 5 | m.CF$_3$ | CH$_3$ | CH$_2$—CH=CH$_2$ | 138 |
| 6 | m.CF$_3$ | CH$_3$ | CH$_2$-φ | 134 |
| 7 | m.CF$_3$ | CH$_3$ | CH$_2$CH$_2$NH$_2$ | 160 |
| 8 | m.CF$_3$ | CH$_3$ | CH$_2$CH$_2$N(CH$_3$)$_2$ | 138 (fumarate) |
| 9 | m.CF$_3$ | H | CH$_3$ | 154 |
| 10 | m.CF$_3$ | H | CH$_2$-φ | 123 |

-continued

| N° | X | R₁ | R | MP, °C. |
|---|---|---|---|---|
| 11 | m.CF₃ | CH₃ | 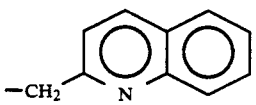 | 189 |
| 12 | m.Cl | CH₃ | CH₃ | 174 |
| 13 | m.CH₃ | CH₃ | CH₃ | 175 |
| 14 | m.F | CH₃ | 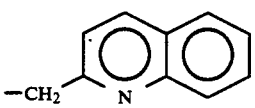 | 177 |
| 15 | p.F | CH₃ | 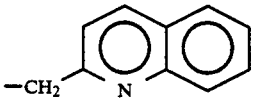 | 190 |
| 16 | 3-4 dimethoxy | H | CH₃ | 107-108 |
| 17 | 3-4-5 trimethoxy | H | CH₃ | 156 |
| 18 | 3-4-5 trimethoxy | CH₃ | CH₃ | 219 |

Experimentation

Various toxicological and pharmacological tests have been carried out on the compounds which are the object of the present invention.

A - Toxicology

The compounds of the invention have been subjected to toxicology evaluation.

The toxicity has been determined as the lethal dose of 50% of the animals tested (LD50). It has been determined on batches of ten mice by the oral route, and computed in accord with the method of Thomson and Weil (Biometrics 8, 249 (1958)).

The LD50's of the compounds tested are greater than 300 mg/kg upon oral administration.

B - Pharmacological Properties

The pharmacological experiments have demonstrated remarkable properties on the central nervous system on the one hand, and in regard to inhibition of lipoxygenase on the other hand.

1 - Anxiolytic Activity

The anxiolytic activity of the compounds of the present invention is demonstrated by means of the Vogel test (M. H. Thiebot et al., Eur. J. Pharma. 88, 111-116 (1987)), and in the X-labyrinth test (elevated plus maze) (S. Pellow et al., J. Neurosci. Methods 14, 149-167 (1985)). Results obtained on the products of the present invention are presented in the following and are expressed in percentage of increase by reference to an untreated control, with the product being administered per os at a dose of 30 mg/kg.

| Product: | Vogel test: | X-labyrinth test: |
|---|---|---|
| 2 | 95% | 95% |
| 5 | 48% | — |
| 6 | 98% | 18% |
| 9 | 52% | 165% |
| 10 | 38% | — |

2 - Inhibition of Lipoxygenase

This activity has been demonstrated by a test of the inhibition of the production of leukotriene B4 on suspensions of polymorphonuclear peritonea of rates stimulated by means of the Ionophore A 23 187.

The results obtained with certain products of the invention are reported, by way of example, in the following:

| Products: | IC₅₀ (μMol): |
|---|---|
| 6 | 1.25 |
| 10 | 25 |
| 11 | 1.10 |

3 - Therapeutic Applications

Based on their pharmacological properties, the compounds of the present invention may be used in human therapeutics in the treatment of various diseases and, most particularly, anxiety, asthma, rheumatic inflammation, inflammatory diseases of both the digestive tract and of the colon, and psoriasis.

Pharmaceutical compositions containing the active principles of the present invention may be prepared in a form for oral, rectal, parenteral, or other administration, for example, in the form of pills, capsules, gels, or solutions containing the active ingredient and one or more appropriate excipients, carriers, or diluents It is likewise possible to associate a compound of the present invention in such a pharmaceutical composition with one or more other active principles which are therapeutically-active and pharmaceutically-acceptable.

A pharmaceutical composition of the invention may accordingly be defined as a pharmaceutical composition useful for the treatment of anxiety, asthma, rheumatic inflammation, an inflammatory disease of the digestive tract or of the colon, or psoriasis which contains, as active principle, an amount of a compound of the present invention which is effective for such purpose.

A method of treating according to the present invention may accordingly be defined as a method of treating anxiety, asthma, rheumatic inflammation, an inflammatory disease of the digestive tract or of the colon, or psoriasis in a mammal afflicted therewith, comprising the step of administering to said mammal an amount of a compound of the invention which is effective for such purpose, preferably in the form of a pharmaceutical composition thereof in which it is present together with a pharmaceutically-acceptable diluent or carrier.

It will of course be apparent to one skilled in the art that the amount of the active ingredient must be an effective anxiolytic or other effective amount and also that the ailment or condition treated must be one which is susceptible to treatment with a compound of the invention, that is, one which is responsive to treatment therewith. The pharmaceutical composition of the invention may, for example, contain between about 10 and about 200 mg of active ingredient per unit dosage form. It will, however, be apparent to one skilled in the art that the exact dosage and dosage form, as well as the particular pharmaceutically-acceptable diluent, carrier, or adjuvant employed, as well as the particular type of pharmaceutical form employed, whether tablet, capsule, suppository, or injectable solution, will be dependent upon the exact condition involved, as well as the condition of the patient involved, and as usual in accord with the preferences and directions of the physician or veterinarian in charge.

It is therefore seen from the foregoing that new compounds, pharmaceutical compositions thereof, a method of treating and ameliorating susceptible ailments or conditions with such a compound or pharmaceutical composition of the invention, and a method of making the same, have all been provided, and that all of the objects of the invention have thus been fulfilled.

It is to be understood that the present invention is not to be limited to the exact compounds, compositions, procedures, or formulations disclosed, as numerous modifications and changes therein will immediately become apparent to one skilled in the art to which this invention pertains, wherefore the present invention is to be understood as limited only by the full scope which can be legally accorded to the appended claims.

We claim:

1. A compound selected from a 3-substituted-1-phenyl-1,4-dihydro-4-oxopyridazine of Formula I:

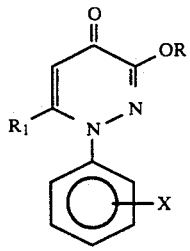

I in which:
"X" represents one or more substituents selected from $C_{1-4}$ alkyloxy, halogen, and trifluoromethyl;
"$R_1$" represents hydrogen or $C_{1-3}$ lower alkyl;
"R" represents
hydrogen;
$C_{1-4}$ lower-alkyl or $C_{2-4}$ alkenyl;
$C_{1-4}$ lower-alkyl; or
aminoalkyl of Formula II:

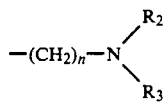

II in which "n" is 2 to 4, inclusive, and
"$R_2$" and "$R_3$", identical or different, represent hydrogen or $C_{1-4}$ lower-alkyl;
phenyl $C_{1-4}$ alkyl, optionally substituted in the aromatic ring by one or more substituents selected from $C_{1-3}$ alkyl, $C_{1-3}$ alkyloxy, halogen, and trifluoromethyl; and
arylmethyl, wherein aryl is selected from 2-pyridyl, 3-pyridyl, 4-pyridyl, and 2-quinolinyl, and a pharmaceutically-acceptable salt thereof when R contains a salt-forming group.

2. A compound of claim 1, selected from the group consisting of:

1-Metatrifluoromethylphenyl-1,4-dihydro-3-hydroxy-4-oxo-6-methylpyridazine;
1-Metatrifluoromethylphenyl-1,4-dihydro-3-methoxy-4-oxo-6-methylpyridazine;
1-Metatrifluoromethylphenyl-1,4-dihydro-3-acetoxy-4-oxo-6-methylpyridazine;
1-Metatrifluoromethylphenyl-1,4-dihydro-3-ethoxy-4-oxo-6-methylpyridazine;
1-Metatrifluoromethylphenyl-1,4-dihydro-3-allyloxy-4-oxo-6-methylpyridazine;
1-Metatrifluoromethylphenyl-1,4-dihydro-3-benzyloxy-4-oxo-6-methylpyridazine;
1-Metatrifluoromethylphenyl-1,4-dihydro-3-$\beta$-aminoethoxy-4-oxo-6-methylpyridazine;
1-Metatrifluoromethylphenyl-1,4-dihydro-3-$\beta$-dimethylaminoethoxy-4-oxo-6-methylpyridazine;
1-Metatrifluoromethylphenyl-1,4-dihydro-3-methoxy-4-oxopyridazine;
1-Metatrifluoromethylphenyl-1,4-dihydro-3-benzyloxy-4-oxopyridazine;
1-Metatrifluoromethylphenyl-1,4-dihydro-3-(2-quinolylmethoxy)-4-oxo-6-methylpyridazine;
1-Metachlorophenyl-1,4-dihydro-3-methoxy-4-oxo-6-methylpyridazine;
1-Metafluorophenyl-1,4-dihydro-3-(2-quinolylmethoxy)-4-oxo-6-methylpyridazine;
1-Parafluorophenyl-1,4-dihydro-3-(2-quinolylmethoxy)-4-oxo-6-methylpyridazine;
1-(3,4-Dimethoxy)phenyl-1,4-dihydro-3-methoxy-4-oxopyridazine;
1-(3,4,5-Trimethoxy)phenyl-1,4-dihydro-3-methoxy-4-oxo-pyridazine;
1-(3,4,5-Trimethoxy)phenyl-1,4-dihydro-3-methoxy-4-oxo-6-methylpyridazine.

3. A pharmaceutical composition useful for the treatment of anxiety which contains, as active principle, an amount of a compound of claim 1 which is effective for such purpose together with a pharmaceutically-acceptable diluent or carrier.

4. A pharmaceutical composition useful for the treatment of anxiety which contains, as active principle, an amount of a compound of claim 2 which is effective for such purpose together with a pharmaceutically-acceptable diluent or carrier.

5. A method of treating anxiety in a mammal afflicted therewith, comprising the step of administering to said mammal an amount of a compound of claim 1 which is effective for such purpose.

6. A method of treating anxiety in a mammal afflicted therewith, comprising the step of administering to said mammal an amount of a compound of claim 2 which is effective for such purpose.

* * * * *

UNITED STATES PATENT AND TRADEMARK OFFICE
CERTIFICATE OF CORRECTION

PATENT NO. : 5,254,554

DATED : October 19, 1993

INVENTOR(S) : Jean-Marie Autin, Dennis Bigg, Jean-Francois Patoiseau.

It is certified that error appears in the above-indentified patent and that said Letters Patent is hereby corrected as shown below:

Title Page, [56], line 4; correct the spelling of "Staehelin".
Title Page, [56], after line 18; insert -- Chemical Abstracts, vol. 51, No. 6, 4379-4384 (1957).
Col. 1, line 34; correct the spelling of "Staehelin".
Col. 1, line 49; change ", the," to -- , then, --.
Col. 5, line 11; insert a hyphen between "6" and "methylpyridazine".
Col. 5, line 29; insert a hyphen between "roform" and "methanol".
Col. 8, first line; correct the spelling of "rats".
Col. 8, line 50; insert a period after the word "diluents".
Col. 9, line 57; insert a colon at the end of the line.
Col. 9, line 60; change "alkyl" to -- acyl --.

Signed and Sealed this

Twenty-fourth Day of May, 1994

Attest:

BRUCE LEHMAN

*Attesting Officer*     *Commissioner of Patents and Trademarks*